United States Patent [19]

Wolters et al.

[11] 4,343,896

[45] Aug. 10, 1982

[54] METHOD AND TEST PACK FOR THE DEMONSTRATION AND DETERMINATION OF AN ANTIGEN OR ANTIBODY

[75] Inventors: Gerrit Wolters; Leonardus P. C. Kuypers, both of Oss, Netherlands

[73] Assignee: Akzona Incorporated, Asheville, N.C.

[21] Appl. No.: 145,297

[22] Filed: May 1, 1980

Related U.S. Application Data

[63] Continuation of Ser. No. 653,579, Jan. 29, 1976, abandoned.

[30] Foreign Application Priority Data

Feb. 1, 1975 [NL] Netherlands .......................... 7501215

[51] Int. Cl.$^3$ ............................................. G01N 33/54
[52] U.S. Cl. ..................................... 435/7; 23/230 B;
422/61; 424/12; 435/810
[58] Field of Search ........................... 435/7; 23/230 B;
424/12; 422/61

[56] References Cited

U.S. PATENT DOCUMENTS

| | | |
|---|---|---|
| Re. 29,169 | 4/1977 | Schuurs . |
| 3,654,090 | 4/1972 | Schuurs . |
| 3,720,760 | 3/1973 | Bennich .................................. 424/1 |
| 3,791,932 | 2/1974 | Schuurs . |
| 3,826,619 | 7/1974 | Bratu . |
| 3,839,153 | 10/1974 | Schuurs . |
| 3,850,752 | 11/1974 | Schuurs . |
| 3,853,987 | 12/1974 | Dreyer . |
| 3,879,262 | 4/1975 | Schuurs . |
| 3,896,217 | 7/1975 | Johnson . |
| 3,935,074 | 1/1976 | Rubenstein . |
| 4,016,043 | 4/1977 | Schuurs . |

OTHER PUBLICATIONS

A. M. Prince et al., The Lancet, 1346–1350, Jun. 16, 1973.
A. R. Midgley, Jr. et al., "Radioimmunoassays Employing Double Antibody Techniques", ACTA ENDOCR. (Kph.) Suppl. 142 at 247–256, (1969).
A. R. Midgley, Jr. et al., "Radioimmunoassay & Steroids," ACTA ENDOCR. II (Kph.), Suppl. 147 at 320–331, (1970).
L. Wide et al., "Radioimmunoassay of Proteins with the Use of Sephddex-Coupled Antibodies," BIOCHEM. BIOPHYS. ACTA 130 at 257–260, (1966).
L. Wide, "Radioimmunoassays Employing Immunosorbents," ACTA ENDOCR. (Kph.) Suppl. 142 at 207–221, (1969).
M. Florkin et al., "Comprehensive Biochemistry," vol. 13, 3rd ed., pp. 62–65, 100, 101, 214–217, 252–253, Elsevier Pub. Co., New York.

*Primary Examiner*—Sidney Marantz
*Attorney, Agent, or Firm*—Robert H. Falk; Charles A. Wendel; Francis W. Young

[57] ABSTRACT

A method for the demonstration and determination of an antigen or antibody in a test fluid, and to a test kit for the application of this method. The determination of the antigen or antibody is performed by utilizing two antibodies raised against the same antigen, but in different animal species. One of the antibodies is labeled. In order to separate the labeled-bound fraction from the labeled-free fraction, an insolubilized antibody directed against the unlabeled antibody is employed. For antigen determination, the unlabeled antibody is the antibody produced from the second animal species; for antibody determination, the unlabeled antibody can be either the antibody to be detected or determined or the antibody produced from the second animal species.

37 Claims, No Drawings

METHOD AND TEST PACK FOR THE DEMONSTRATION AND DETERMINATION OF AN ANTIGEN OR ANTIBODY

This is a continuation of application Ser. No. 653,579, filed Jan. 29, 1976, abandoned.

BACKGROUND OF THE INVENTION

A number of methods for the demonstration and determination of antigens and antibodies are already known, such methods making use of the immunological affinity between these components.

When using labelled components, one of the best known methods is the so-called Sandwich technique, in which, for the demonstration and determination of, for example, an antigen in a test-fluid, this antigen is incubated with a certain quantity of labelled, for example, radioactive antibody directed against this antigen, and with a certain quantity of an antibody, rendered insoluble, also directed against the antigen to be determined. After termination of the immunological reaction, the radioactivity in the liquid or solid phase is measured, the said radioactivity being a measure of the amount of the antigen to be determined.

This method, just as the other customary techniques, has the major disadvantage that one of the reaction components in the main reaction of this immunological estimation is in an insoluble form, as a result of which the affinity for the binding partner decreases, and the sensitivity and accuracy of the test system are, therefore, adversely affected.

In order to increase the sensitivity, this insoluble component ought to be used in relatively large quantities, which is a major disadvantage for economic reasons, since most antibodies are particularly expensive.

An immunological method for the demonstration and determination of antigens and antibodies, in which the reaction between antigen and antibody is a reaction of soluble components, such that the sensitivity is considerably increased, and in which a separation into solid and liquid phases, by using an insoluble immunoadsorbent, is still obtained, has now been found; although the method is immunologically specific for one of the reaction components it is still possible to make an arbitrary choice within a certain group of substances.

DESCRIPTION OF THE INVENTION

In the method according to the invention, the fluid to be tested, containing an antigen or an antibody, is brought into contact with a certain quantity of the corresponding binding partner of the component to be estimated, a certain quantity of a second antibody directed against the antigen-component present, said second antibody having been produced in an animal species other than that used for the production of the antibody-component added or to be tested, and a certain quantity of an antibody, rendered insoluble, directed against one of the two aforementioned antibody-components, whereby the other antibody is or has been labelled, after which the mixture is incubated and the amount of labelled component in the liquid or solid phase is determined, the said amount being a measure of the amount of the component to be estimated. The method also permits one to detect the presence of the component.

The labelling of one of the reaction components can be brought about by incorporation of a radioactive atom or group, or by coupling this component to an enzyme, a dyestuff or a fluorescent group.

This labelling is usually performed before the immunological reaction according to the invention, but it may also be performed in a later stage, by allowing the component which must be labelled to react with the corresponding binding partner, which has been radioactively labelled or which has been coupled to an enzyme, dyestuff or fluorescent group.

The components concerned are preferably labelled by coupling to an enzyme, since the estimation of this is much simpler than for example, the estimation of radioactivity, for which special apparatus and expert personnel are necessary.

The enzymes used are preferably those which can be colorimetrically, spectrophotometrically, or fluorimetrically determined. In particular, enzymes from the group of oxidoreductases, such as catalase, peroxidase, glucose oxidase, $\beta$-glucuronidase, $\beta$-D-glucosidase, $\beta$-D-galactosidase, urease and galactose oxidase, receive consideration.

The coupling of the enzyme and the immunological component can be brought about in a known way, for example, by the formation of an amide linkage by methods known from peptide chemistry.

The labelling with a radioactive isotope can also be performed in a known way. Isotopes useful for labelling are predominantly $I^{125}$, $I^{131}$, $C^{14}$, and $H^3$.

As described above, the method according to the invention is useful for the demonstration of both antigens and antibodies, with the proviso that when the method is used for antigens, the said antigens must be at least bivalent, i.e., they must be able to bind more than one antibody.

Plasma proteins, enzymes and protein or peptide hormones such as gonadotrophic hormones, insulin and ACTH, as well as viruses such as hepatitis virus, can be named as examples of antigens.

For the demonstration and determination of an antigen in a test liquid, the antigen concerned is incubated with a first antibody, with specificity for this antigen, which has been produced in a certain animal species, and a second antibody, with specificity for the same antigen, that has been produced in an animal species other than that used for the production of the first antibody.

The first antibody is labelled, either prior to or in a later stage of the immunological reaction, according to one of the methods described above.

The antibody, which has been rendered insoluble and which possesses specificity for one of the above-named antibodies, can be added to the test medium at the same time as the other components, but may also be added after the antigen and the antibodies have been incubated for some time.

Incubation usually takes place at a temperature between 0° C. and 56° C., and the incubation time does not usually exceed three hours.

The method for the detection or determination of an at least bivalent antigen in a fluid can be made by the use of a test pack, comprising:

(a) a given amount of a first antibody against the antigen to be detected or determined.

(b) a given amount of a labeled second antibody against said antigen to be detected or determined, said second antibody being produced in a different animal species than the first antibody; and (c) a given amount of an insolubilized third antibody against said first antibody.

In the alternative, the test pack may comprise:

(a) a given amount of a first antibody against the antigen to be detected or determined;

(b) a given amount of a second antibody against said antigen, said second antibody being produced in a different animal species than the first antibody;

(c) a given amount of a labeled third antibody against said second antibody; and (d) a given amount of an insolubilized fourth antibody against said first antibody.

The antibodies can be obtained by injecting serum, or the globulin-fraction of this serum, from the animal in which the second antibody has been produced into another sort of animal and isolating the thus-formed antibodies fraction. This anti-antibody fraction is a universal reagent, since it does not react specifically with a particular antibody but possesses affinity for every antibody produced in the animal species concerned. Herein resides one of the major advantages of the method according to the invention, since it is now not necessary to use an expensive antibody in relatively large quantities as immunoadsorbent, as with the usual techniques, but a universal anti-antibody fraction which can be obtained more easily by injection of the immunoglobulin fraction of the animal species in which the second antibody has been produced into another animal. Furthermore, the choice of the animal species for the provision of the serum or the immunoglobulin fraction thereof is unrestricted, since no restrictions are placed on the choice of the animal species in which the second antibody can be produced.

Rendering the anti-antibody fraction insoluble in order to obtain an immunoadsorbent can be realized by cross-linking, by adsorption or by covalently bonding to a solid carrier, such as cellulose, agarose, cross-linked dextran, polystyrene, polymers with hydroxyl and/or amino groups and suchlike.

The bonding can be brought about in a known way, for example, by coupling with a carbodiimide, glutaraldehyde, or cyanogen bromide, by diazotizing or with di- and tri-chloro-s-triazines.

An elegant method of rendering the anti-antibody insoluble consists of coupling the said anti-antibody fraction to a tube of polymeric material, such as polystyrene, by means of adsorption or covalent bonding. After incubation with the test liquid and the other components, separation of the liquid and solid phases can readily be obtained by removing the liquid from the tube.

The quantities of antibody and immuno-adsorbent to be used can be determined empirically, and the amount of antigen to be estimated which corresponds to the activity of the labelled component found in the liquid or solid phase can be determined by means of calibration curves.

For the determination of an antibody in test liquids, the procedure followed is analogous to that given above for the demonstration and determination of an antigen, the only difference being that an antigen is now added together with a labelled antibody with specificity for this antigen, which antibody has been produced in an animal species other than the species from which the antibody to be determined has been obtained. See Example I.

The method for the detection or determination of an antibody in a fluid sample can be made by a test pack, comprising:

(a) a given amount of an antigen for which the antibody to be detected or determined possesses affinity;

(b) a given amount of a labeled second antibody, said second antibody being produced in a different animal species than the antibody to be detected or determined; and (c) a given amount of an insolubilized third antibody against the antibody to be determined.

In the alternative, the test pack may comprise:

(a) a given amount of an antigen for which the antibody to be detected or determined possesses affinity;

(b) a given amount of a second antibody, said second antibody being produced in a different animal species than the antibody to be detected or determined;

(c) a given amount of a labeled third antibody against either the antibody to be detected or determined or the second antibody; and (d) a given amount of an insolubilized fourth antibody directed against the other of the two antibodies to which the labeled antibody in (c) is directed.

The method herein described is also important for the demonstration of immune complexes, which cannot be demonstrated with the techniques at present known. See Example III.

The invention is further illustrated by means of the following examples.

EXAMPLE I

DEMONSTRATION OF ANTIBODIES AGAINST RUBELLA VIRUS IN HUMAN SERUM 0.50 ml. of a test sample (human serum), 0.25 ml. of a suitable quantity of inactivated rubella virus (previously determined) suspended in 0.15 M phosphate buffer (pH 6.9) and 0.25 ml. of a rabbit anti-(rubella virus) serum, appropriately diluted in 0.15 phosphate buffer (pH 6.9) in accordance with the quantity of inactivated rubella virus, are consecutively added to a polystyrene tube, onto which sheep anti-(rabbit-$\gamma$-globulin) has been adsorbed, after which the reaction mixture is incubated at 37° C. for one hour.

The tube is then emptied by suction and 1 ml. of a sheep (anti-human-$\gamma$-globulin)-$\gamma$-globulin fraction, labelled with HRP (horse-radish peroxidase), at a particular concentration in 0.15 M phosphate buffer, (pH 6.9) is added, after which the reaction mixture is incubated at 37° C. for one hour.

The tube is emptied by suction and washed 3 times with 2 ml. aliquots of 0.15 M phosphate buffer, pH 6.2.

2 ml. of a solution of ortho-phenylene-diamine (0.2 mg./ml.) in 0.15 M phosphate buffer, containing 0.01% $H_2O_2$, is now added to the tube. The reaction mixture is incubated at room temperature for one hour, after which the reaction is stopped by the addition of 0.5 ml. N $H_2SO_4$.

After the test has been performed, the extinctions of serial dilutions of a human serum containing antibodies against rubella virus, and a human serum free from these antibodies, are measured at 492 nm.

| Sample | Undiluted | | | | | | |
|---|---|---|---|---|---|---|---|
| Positive | 0.963 | 0.583 | 0.322 | 0.185 | 0.111 | 0.075 | 0.053 |
| Negative | 0.050 | 0.045 | 0.043 | 0.044 | 0.042 | 0.040 | 0.039 |

| Sample | Undiluted |
|---|---|
| Buffer | 0.040 |

EXAMPLE II

DEMONSTRATION OF HEPATITIS B ANTIGEN (HBAg) IN HUMAN SERUM 0.9 ml. of a mixture of: (a) a previously determined amount of sheep-antibodies against HBAg, labelled with HRP and (b) an equivalent amount of rabbit antibodies against HBAg, dissolved in phosphate buffer (pH 6.9) containing 0.9% NaCl and 0.1% bovine serum albumen, is added to 0.1 ml. of test sample (consisting of human serum).

The reaction mixture is incubated at room temperature for one hour, after which 0.5 ml. of a suspension of cellulose, to which sheep anti-(rabbit-$\gamma$-globulin) has been coupled in a concentration of about 6 mg/ml., is added. The reaction mixture is shaken at room temperature for one hour.

The cellulose is precipitated by means of a centrifugation and washed three times with 5 ml. portions of the above-mentioned buffer. The enzyme reaction is performed with the sediment, as described in Example 1.

If the extinction measured at 492 nm., after subtraction of the blank, is more than twice that of a control serum containing no HBAg, then the sample is considered positive for HBAg.

EXAMPLE III

DEMONSTRATION OF IMMUNE COMPLEXES OF HBAg AND ANTI-HBAg IN HUMAN SERUM 0.9 ml. of a rabbit anti-HBAg serum diluted 1:1000 in 0.15 M phosphate buffer (pH 6.9) is added to 0.1 ml. of a test sample, after which the mixture is incubated at 37° C. for one hour.

1 ml. of a 1:100 dilution of the $\alpha$-globulin fraction of a sheep anti-(human-$\gamma$-globulin) serum, onto which HRP has been coupled, is added to the reaction mixture, which is then incubated at 37° C. for a further hour.

3 mg. cellulose, to which sheep antibodies against rabbit $\gamma$-globulin have been bound, is added to the reaction mixture, which is then incubated with repeated tilting at room temperature for one hour.

The cellulose is subsequently sedimented by means of centrifugation and washed three times with 5 ml. aliquots of the above-mentioned buffer. The enzyme reaction, as described in Example I, is performed with the sediment.

The following is an example of the reaction of a test-sample of human serum, diluted in another human serum which is free from HBAg, anti-HBAg or immune complexes thereof:

| Undiluted | $\frac{1}{2}$ | $\frac{1}{4}$ | $\frac{1}{8}$ | 1/16 | 1/32 | 1/64 |
|---|---|---|---|---|---|---|
| 0.035 | 0.987 | 0.873 | 0.465 | 0.259 | 0.107 | 0.072 |
| Negative sample 0.052 | | | | | | |

EXAMPLE IV

DEMONSTRATION OF HUMAN CHORIONIC GONADOTROPHIN IN BIOLOGICAL FLUIDS OF HUMAN ORIGIN

To a polystyrene tube, onto which sheep antibodies against rabbit $\gamma$-globulin have been adsorbed, is consecutively added:

1 ml. sample (for example, human urine)
0.1 ml. of a mixture of:
(a) a previously-determined quantity of sheep antibodies against HCG, which have been labelled with HRP; and
(b) an equivalent quantity of rabbit antibodies against HCG, dissolved in a pH 6.4 buffer which contains 0.5 M phosphate, 0.9% NaCl and 1% bovine serum albumen.

The reaction mixture is incubated at room temperature for one hour.

The tube is then emptied by suction and washed three times with 2 ml. aliquots of 0.1 M phosphate, pH 6.0, after which the enzyme reaction is performed as described in Example I.

If a reference sample containing 10 i.u. HCG per liter in 0.01 M phosphate buffer (pH 6.0), and a sample of man's urine as blank, are tested alongside a sample of woman's urine, it can be determined whether the woman concerned was possibly pregnant. This would be the case if the measured extinction of the test sample was higher than that of the reference sample, after correction for the blank value.

EXAMPLE V

DETERMINATION OF THE CONTENT OF THE THIRD COMPONENT (C3) IN HUMAN SERUM

Polystyrene tubes are covered on the inside with horse antibodies against rabbit-$\gamma$-globulin. A series of dilutions (1:1000, 3:1000, 1:200 and 1:100) of a normal human serum (reference serum), of known C3-content, are made in 0.1 M phosphate buffer, pH 7.4.

Subsequently, 10 $\mu$l of each serum dilution, and 0.5 ml. of a 0.1 M phosphate buffer (pH 7.4) containing 0.01 M ethylenediamine tetraacetate (EDTA) and 1% bovine serum albumin, are placed in tubes as described above.

0.5 ml. of a solution of rabbit antibodies against human C3, in 0.1 M phosphate buffer (pH 7.4) containing 0.01 EDTA and 1% bovine serum albumin, is then added to each tube and the mixture is incubated at 37° C. for one hour.

The liquid phase is removed and the tube is washed 4 times with 2 ml. aliquots of 0.1 M phosphate buffer (pH 7.4) containing 0.01 M EDTA.

1 ml. of a solution of a previously determined quantity of horse antibodies against human C3 in 0.1 M phosphate buffer (pH 7.4) containing 1% bovine serum albumin, the said antibodies having been labelled with HRP, is then added to the empty tube.

After incubation at 37° C. for 1 hour, the liquid phase is removed and the tube is washed 4 times with 0.1 M phosphate buffer (pH 7.4). The amount of enzyme activity bound to the tube is finally determined as described in Example I.

By plotting the extinction measured at 492 nm against the concentration of the serum, a correlation between extinction and C3-content is obtained.

Using this test system, it can be determined whether the C3 content of an unknown serum sample is reduced in relation to the reference system. Furthermore, the concentration of C3 in the unknown sample can be represented in terms of the concentration of C3 in the reference serum.

We claim:

1. A process for the detection or determination of an at least bivalent antigen in a liquid sample, said process comprising the steps of:
   (a) providing a given quantity of a first antibody against said at least bivalent antigen to be detected or determined, which first antibody is or has been labeled;
   (b) providing a given quantity of a second antibody against said at least bivalent antigen to be detected or determined, said second antibody being produced in a different animal species than said first antibody;
   (c) providing a given quantity of an insolubilized third antibody against said second antibody;
   (d) contacting and incubating a sample of a liquid containing said at least bivalent antigen to be detected or determined with the components of steps (a), (b), and (c) to form a reaction mixture having a liquid phase and a solid phase;
   (e) separating the liquid phase from the solid phase; and
   (f) detecting or determining the labeled component in either the liquid phase or the solid phase, which detection or determination is a measure of the presence of quantity of said at least bivalent antigen to be detected or determined.

2. The process of claim 1 wherein the insolubilized third antibody is attached to the reaction surface of a polystyrene test tube.

3. The process of claim 1 wherein the antigen is a hepatitis associated antigen.

4. The process of claim 1 wherein the first antibody is labelled by adding a labelled fourth antibody against said first antibody.

5. The process of claims 1 or 4 wherein the label is a radioactive isotope or an enzyme.

6. A process for the detection or determination of an antibody in a liquid sample, said process comprising the steps of:
   (a) providing a given quantity of an antigen against which an antibody to be detected or determined is directed;
   (b) providing a given quantity of a second antibody against said antigen, said second antibody being produced in a different animal species than said antibody to be detected or determined, whereby either said antibody to be detected or determined or said second antibody is or has been labeled;
   (c) providing a given quantity of an insolubilized third antibody against the non-labeled antibody;
   (d) contacting and incubating the components of steps (a), (b), and (c) with a liquid sample containing said antibody to be detected or determined, to form a reaction mixture having a solid phase and a liquid phase;
   (e) separating the solid phase from the liquid phase; and
   (f) detecting or determining the labeled component in either the liquid phase or the solid phase, which detection or determination is a measure of the presence or quantity of said antibody to be detected or determined.

7. The process of claim 6 wherein the first antibody is directed against rubella virus.

8. The process of claim 6 wherein either the first antibody or the second antibody is labelled by adding a labelled fourth antibody against said first or second antibody.

9. The process of claims 6 or 8 wherein the label is a radioactive isotope or an enzyme.

10. A test pack for the detection or determination of an at least bivalent antigen in a fluid sample comprising:
    a. a given amount of a first antibody against the at least bivalent antigen to be detected or determined;
    b. a given amount of a labelled second antibody against said at least bivalent antigen, said second antibody being produced in a different animal species than the first antibody;
    c. a given amount of an insolubilized third antibody against said first antibody.

11. A test pack for the detection or determination of an at least bivalent antigen in a fluid sample comprising:
    a. a given amount of a first antibody against the at least bivalent antigen to be directed or determined;
    b. a given amount of a second antibody against said at least bivalent antigen, said second antibody being produced in a different animal species than the first antibody;
    c. a given amount of a labelled third antibody against said second antibody;
    d. a given amount of an insolubilized fourth antibody against said first antibody.

12. A test pack for the detection or determination of an antibody in a fluid sample, comprising:
    a. a given amount of an antigen for which the antibody to be detected or determined possesses affinity;
    b. a given amount of a labelled second antibody, said second antibody being produced in a different animal species than the antibody to be detected or determined;
    c. a given amount of an insolubilized third antibody against the antibody to be detected or determined.

13. A test pack for the detection or determination of an antibody in a fluid sample comprising:
    a. a given amount of an antigen for which the antibody to be detected or determined possesses affinity;
    b. a given amount of a second antibody, said second antibody being produced in a different animal species than the antibody to be detected or determined;
    c. a given amount of a labelled third antibody against either the antibody to be detected or determined or the second antibody;
    d. a given amount of an insolubilized fourth antibody directed against the other of the two antibodies to which the labelled third antibody in (c) is directed.

14. A process for the detection or determination of an at least bivalent antigen in a liquid sample, said process comprising the steps of:
    (a) providing a given quantity of a first antibody against said at least bivalent antigen to be detected or determined, which antibody is or has been labeled, said given quantity being at least immunochemically equivalent to the maximum amount of said at least bivalent antigen to be detected or determined;

(b) providing a given quantity of a second antibody against said at least bivalent antigen to be detected or determined, said second antibody being produced in a different animal species than said first antibody, said given quantity being at least immunochemically equivalent to the maximum amount of said at least bivalent antigen to be detected or determined;

(c) providing a given quantity of an insolubilized third antibody against said second antibody, said given quantity being at least immunochemically equivalent to the maximum amount of said second antibody provided in step (b);

(d) contacting and incubating a sample of a liquid containing said at least bivalent antigen to be detected or determined with the components of steps (a), (b), and (c) to form a reaction mixture having a liquid phase and a solid phase;

(e) separating the liquid phase from the solid phase; and (f) detecting or determining the labeled component in either the liquid phase or the solid phase, which detection or determination is a measure of the presence or quantity of said at least bivalent antigen to be detected or determined.

15. The process of claim 14, wherein said first antibody is labeled with horseradish peroxidase.

16. The process of claim 14, wherein said at least bivalent antigen is human chorionic gonadotrophin.

17. The process of claim 14, further comprising the steps of:
first, contacting and incubating components (a) and (b) with the liquid sample containing said at least bivalent antigen to be detected or determined to form an intermediate reaction mixture; and
contacting and incubating said intermediate reaction mixture with the insolubilized third antibody of step (c) in the manner recited in step (d).

18. The process of claim 14, further comprising the steps of:
first, contacting and incubating the second antibody provided in step (b) with the liquid sample containing said at least bivalent antigen to be detected or determined to form a first intermediate reaction mixture;
second, contacting and incubating said first intermediate reaction mixture with the labeled antibody provided in step (a) to form a second intermediate reaction mixture; and
third contacting and incubating said second intermediate reaction mixture with the insolubilized third antibody provided in step (c) in the manner recited in step (d).

19. The process of claim 14, further comprising the steps of:
first, contacting and incubating the insolubilized third antibody of step (c) with the liquid sample containing said at least bivalent antigen to be detected or determined and said second antibody of step (b) to form an intermediate reaction mixture having an intermediate solid phase and an intermediate liquid phase;
second, separating the intermediate solid phase from the intermediate liquid phase; and
third, contacting and incubating the intermediate solid phase with the labeled first antibody provided in step (a) in the manner recited in step (d).

20. The process of any of claims 17, 18, or 19, wherein said at least bivalent antigen is hepatitis B surface antigen.

21. The process of any of claims 17, 18, or 19, wherein said at least bivalent antigen is human chorionic gonadotrophin.

22. The process of any of claims 17, 18, or 19, wherein said at least bivalent antigen is the third component in human serum.

23. The process of any of claims 17, 18, or 19, wherein said first antibody provided in step (a) is labeled with an enzyme.

24. The process of claim 14, wherein said insolubilized third antibody of step (c) is in suspension.

25. The process of claim 24, wherein said insolubilized third antibody is in a suspension of cellulose.

26. The process of claim 24, wherein said at least bivalent antigen is HBAg.

27. The process of claim 24, wherein the given quantities of said first antibody (a) and said second antibody (b) are immunochemically equivalent.

28. The process of claim 24, further comprising the steps of:
first, contacting and incubating components (a) and (c) with the liquid sample containing the antibody to be detected or determined to form an intermediate solid phase and an intermediate liquid phase;
separating the intermediate solid phase and the intermediate liquid phase; and
contacting and incubating said intermediate solid phase with the labeled second antibody of step (b) in the manner recited in step (d).

29. A test pack for the detection or determination of an at least bivalent antigen to be detected or determined in a liquid sample according to the method of claims 14, 17, 18, or 19, comprising:
(a) a given quantity of a first antibody against the at least bivalent antigen to be detected or determined, said given quantity being at least immunochemically equivalent to the maximum amount of said at least bivalent antigen to be detected or determined;
(b) a given quantity of a second antibody against said at least bivalent antigen to be detected or determined, said second antibody being produced in a different animal species than said first antibody, said given quantity of second antibody being at least immunochemically equivalent to the maximum amount of said at least bivalent antigen to be detected or determined; and
(c) a given quantity of an insolubilized third antibody against said second antibody, said given quantity being at least immunochemically equivalent to the maximum amount of second antibody in (b).

30. The test pack of claim 29, where the given quantities of said first antibody and said second antibody are immunochemically equivalent.

31. A process for the detection or determination of an antibody in a liquid sample, said process comprising the steps of:
(a) providing a given quantity of an antigen against which an antibody to be detected or determined is directed, said given quantity being at least immunochemically equivalent to the maximum amount of antibody to be detected or determined;
(b) providing a given quantity of a second antibody against said antigen, said second antibody being produced in a different animal species than said antibody to be detected or determined, and whereby said second antibody is or has been labeled, said given quantity of second labeled antibody being at least immunochemically equivalent to the maximum amount of antigen provided in step (a);

(c) providing a given quantity of an insolubilized third antibody against the antibody to be detected or determined, said given quantity being at least immunochemically equivalent to the maximum amount of said antibody to be detected or determined;

(d) contacting and incubating the components of steps (a), (b), and (c) with a liquid sample containing said antibody to be detected or determined, to form a reaction mixture having a solid phase and a liquid phase;

(e) separating the solid phase from the liquid phase; and (f) detecting or determining the labeled component in either the liquid or the solid phase, which detection or determination is a measure of the presence or quantity of said antibody to be detected or determined.

32. A test pack for the detection or determination of an antibody in a liquid sample according to the method of claims 31 or 28, comprising:

(a) a given quantity of an antigen against which an antibody to be detected or determined is directed, said given quantity being at least immunochemically equivalent to the maximum amount of said antibody to be detected or determined;

(b) a given quantity of a second antibody against said antigen, said second antibody being produced in a different animal species than said antibody to be detected or determined, whereby said second antibody is or has been labeled and said given quantity of second labeled antibody being at least immunochemically equivalent to the maximum of said antigen in (a); and (c) a given quantity of insolubilized third antibody against the antibody to be detected or determined, said given quantity of insolubilized antibody being at least immunochemically equivalent to the maximum amount of said antibody to be detected or determined.

33. The process of claim 31, wherein said antibody to be detected or determined is an antibody against rubella virus.

34. The process of claim 31, wherein the third antibody is adsorbed to a tube.

35. The process of claim 34, wherein said tube is a polystyrene tube.

36. The process of claim 31, wherein said second antibody is labeled with an enzyme.

37. The process of claim 36, wherein said enzyme is horseradish peroxidase.

* * * * *